(12) United States Patent
Kagawa et al.

(10) Patent No.: US 8,691,949 B2
(45) Date of Patent: Apr. 8, 2014

(54) PEPTIDE HAVING ANTI-DIABETIC ACTIVITY AND USE THEREOF

(75) Inventors: Kyoichi Kagawa, Osaka (JP); Chizuko Fukuhama, Osaka (JP); Chunning Tong, Osaka (JP); Yuka Sasakawa, Osaka (JP)

(73) Assignee: MG Pharma Inc., Osaka (JP)

( * ) Notice: Subject to any disclaimer, the term of this patent is extended or adjusted under 35 U.S.C. 154(b) by 170 days.

(21) Appl. No.: 13/123,784

(22) PCT Filed: Oct. 28, 2009

(86) PCT No.: PCT/JP2009/068504
§ 371 (c)(1),
(2), (4) Date: Apr. 12, 2011

(87) PCT Pub. No.: WO2010/050508
PCT Pub. Date: May 6, 2010

(65) Prior Publication Data
US 2011/0201551 A1 Aug. 18, 2011

(30) Foreign Application Priority Data
Oct. 30, 2008 (JP) ................................ 2008-280031

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *A61P 3/10* | (2006.01) |
| *A61P 7/12* | (2006.01) |
| *A61P 3/08* | (2006.01) |
| *A61K 38/28* | (2006.01) |
| *A61K 51/00* | (2006.01) |

(52) U.S. Cl.
USPC ............ 530/330; 530/333; 530/344; 514/7.3; 514/6.8; 514/6.9; 514/1.1; 424/1.69

(58) Field of Classification Search
None
See application file for complete search history.

(56) References Cited

U.S. PATENT DOCUMENTS

| | | | |
|---|---|---|---|
| 7,541,430 B2 | 6/2009 | Sensfuss et al. | |
| 2005/0014689 A1 | 1/2005 | Sugaru et al. | |
| 2007/0244054 A1 | 10/2007 | Sensfuss et al. | |
| 2009/0088388 A1 | 4/2009 | Sensfuss et al. | |
| 2009/0155376 A1 | 6/2009 | Kagawa et al. | |
| 2011/0113053 A1* | 5/2011 | Khan et al. | 707/769 |
| 2011/0201551 A1* | 8/2011 | Kagawa et al. | 514/6.7 |

FOREIGN PATENT DOCUMENTS

| | | | | |
|---|---|---|---|---|
| EP | 2109054 | * | 10/2009 | ............. G06F 19/00 |
| JP | 2007-524584 A | | 8/2007 | |
| JP | 2008-519758 A | | 6/2008 | |
| WO | 03/002594 | | 1/2003 | |
| WO | 03/030936 A1 | | 4/2003 | |
| WO | 2004/099246 | | 5/2004 | |
| WO | 2006/052031 | | 5/2006 | |
| WO | 2009/126037 A1 | | 10/2009 | |
| WO | WO 2009126037 | * | 10/2009 | ............. G06F 17/38 |

OTHER PUBLICATIONS

Saishin Igaku Daijiten, 1987, p. 1211, Ishiyaku Publishers Inc., Japan.
Atarashii Tonyobyo Chiryoyaku (New Diabetic Medicines), pp. 90-99, 1994, Iyaku (Medicine and Drug) Journal Co., Ltd., Japan.
Joslin's Diabetes mellitus, 13th ed., pp. 521-522, 1994.
International Search Report, PCT/JP2009/068504, dated Dec. 1, 2009.
Sasakawa, Y. et al., II. Effect of globin digest on blood glucose and serum insulin—Type 2 diabetes, Japanese Pharmacology and Therapeutics, 2008, vol. 36, No. 11, pp. 1045-1050.
Nakaoka, F. et al., Anti-diabetic effects of globin digest and its active ingredient Leu-Ser-Glu-Leu in ICR mice, streptozotocin-induced diabetic mice and KK-Ay mice, Life Sciences, 2010, vol. 86, No. 11-12, pp. 424-434.
Supplementary European Search Report dated Feb. 20, 2012, from the European Patent Office in corresponding European Application No. 09823618.5.

\* cited by examiner

*Primary Examiner* — Maury Audet
(74) *Attorney, Agent, or Firm* — Roylance, Abrams, Berdo & Goodman, L.L.P.

(57) ABSTRACT

The present invention provides a composition (a blood glucose increase inhibitor) that has an effect of lowering blood glucose level in a hyperglycemic patient and that is therefore used to reduce blood glucose level in the patient. The present invention further provides a composition that is used to prevent or treat diseases caused by hyperglycemia, in particular, diabetes and diabetic complications (a composition for preventing or treating diseases caused by hyperglycemia, an antidiabetic), based on the above-mentioned effect. A feature of the present invention is using a peptide consisting of the amino acid sequence of Leu-Ser-Glu-Leu as an active ingredient.

3 Claims, 4 Drawing Sheets

Fig. 1

(A: animal, F: fish, P: plant)

| Serial No | Class | Origin (scientific name) | Origin / Japanese (English) |
|---|---|---|---|
| 1 | A | Oryctolagus cuniculus | usagi (rabit) |
| 2 | A | Bos primigenius taurus | ushi (cow) |
| 3 | A | Bos primigenius indicus | ushi (cow) |
| 4 | A | Equus caballus | uma (horse) |
| 5 | A | Meleagris gallopavo | shichimencho (turkey) |
| 6 | A | Gallus gallus | niwatori (chicken) |
| 7 | A | Sus scrofa domestica | buta (pig) |
| 8 | F | Megabalanus rosa | akafujitsubo |
| 9 | F | Squalus acanthias | aburatunozame |
| 10 | F | Gasterosteus aculeatus | itoyo (three-spined stickleback) |
| 11 | F | Uca pugilator | shiomaneki (crab) |
| 12 | F | Lateolabrax japonicus | suzuki (Japanese seaperch) |
| 13 | F | Gadus morhua | taiseiyoumadada |
| 14 | F | Tilapia nilotica | terapia (tilapia) |
| 15 | F | Takifugu rubripes | torafugi (tiger puffer) |
| 16 | F | Oncorhynchus mykiss | nijimasu (rainbow trout) |
| 17 | F | Oncorhynchus nerka | himemasu (red salmon) |
| 18 | F | Paralichthys olivaceus | hirame (olive flounder) |
| 19 | F | Seriola quinqueradiata | buri (yellow-tail) |
| 20 | F | Chrysophrys major | madai (red sea bream) |
| 21 | F | Lampetra japonica | yatsumeunagi (lamprey) |
| 22 | F | Sparus aurata | yoroppahedai (gilthead sea bream) |
| 23 | F | Lymnaea stagnalis | yoroppa-monoaragai (stagnant pond snail) |
| 24 | F | Oikopleura dioica | wakareotamaboya |
| 25 | P | Fragaria x ananassa | ichigo (strawberry) |
| 26 | P | Oryza sativa | ine (rice) |
| 27 | P | Phaseolus vulgaris | ingen-mame (kidney bean) |
| 28 | P | Pisum sativum | endo-mame (peas) |
| 29 | P | Coptis japonica(Japanese goldthread) | ohren (goldthread) |
| 30 | P | Hordeum vulgare distichum | omugi (barley) |
| 31 | P | Betula verrucosa | kabanoki (birch) |
| 32 | P | Chelidonium majus | kusanoou (swallowwort) |
| 33 | P | Citrus paradisi | gurepu-furutsu (grapefruit) |
| 34 | P | Solanum chacoense(Chaco potato) | konafubuki (potato) |
| 35 | P | Ipomoea batatas | satsumaimo (sweet potato) |
| 36 | P | Saccharum sp. | satoukibi (sugarcane) |
| 37 | P | Psophocarpus tetregonolobus | shikakumame (winged beans) |
| 38 | P | Brassica napus | seiyo-aburana (rapeseed) |
| 39 | P | Pyrus communis | seiyo-nashi (pear) |
| 40 | P | Glycine max | daizu (soybeans) |
| 41 | P | Glycine soja(Wild soya bean) | daizu (soybeans) |
| 42 | P | Medicago truncatula | taruumagoyashi (pasture grass) |
| 43 | P | Crepis palaestina | tanpopo (dandelion) |
| 44 | P | Zea mays | tomorokoshi (corn) |
| 45 | P | Lycopersicon esculentum | tomato (tomato) |
| 46 | P | Tricholoma fulvocastaneum | nise-matsutake |
| 47 | P | Gracilaria tenuistipitata liui | nori (dried seaweed) |
| 48 | P | Rosa gallica | bara (rose) |
| 49 | P | Corylus avellana | hezerunattsu (hazelnut) |
| 50 | P | Spinacia oleracea | horenso (spinach) |
| 51 | P | Cucumis melo | meron (melon) |
| 52 | P | Prunus persica | momono-no-ha (mature peach leaf) |

PEPTIDE HAVING ANTI-DIABETIC ACTIVITY AND USE THEREOF

TECHNICAL FIELD

The present invention relates to a novel peptide that has an inhibitory effect on an increase in blood glucose level, and an insulin secretion-enhancing effect. Further, the present invention relates to uses of the peptide that has the above-mentioned pharmacological effects.

BACKGROUND ART

The blood glucose level in the body is controlled by the balance between the hypoglycemic action of insulin and the blood glucose-increasing action of adrenalin, glucagon, glucocorticoid, etc. More specifically, insulin inhibits glycogenolysis and gluconeogenesis in the liver to suppress the production of glucose and reduce the amount of glucose released from the liver into the blood; and, at the same time, insulin increases glucose uptake into skeletal muscles and white adipose tissues, thereby lowering the blood glucose level. In contrast, adrenalin, glucagon, etc. promote glycogenolysis and gluconeogenesis in the liver and enhance glucose release therefrom, thereby increasing the blood glucose level.

Diabetes is a metabolic disease in which a hyperglycemic state persists due to an acute or chronical decrease in the action of insulin, resulting in disorders of sugar metabolism, lipid metabolism, amino acid metabolism, etc.

Diabetes is categorized as either insulin-dependent or non-insulin-dependent. To treat patients with insulin-dependent diabetes (type 1 diabetes mellitus), whose insulin secretory capacity is reduced or lost, dietary therapy and oral hypoglycemic agents are ineffective, and the administration of insulin is the only treatment. In contrast, to treat patients with non-insulin-dependent diabetes, who account for 90 percent of diabetic patients, although their insulin action is low compared with that of normal people, the administration of insulin is not always required, and alimentary therapy and exercise therapy are usually performed. When these therapies are not sufficient, chemotherapy by hypoglycemic agents is used concomitantly.

As described above, diabetes is a disease resulting in metabolic disorders due to a persistent hyperglycemic condition. Therefore, it is a troublesome disease that may be accompanied by many complications in the eyes, kidneys, nervous system, cardiovascular system, skin, etc. Such complications are generally considered to be decreased by controlling the blood glucose level to near normal levels (Non-Patent Literature (NPL) 1).

Known pharmaceutical preparations for ameliorating a hyperglycemic condition include insulin preparations, sulfonylurea preparations, biguanide preparations, insulin resistance improvers, α-glucosidase inhibitors, etc. Insulin preparations are therapeutic agents for insulin-dependent diabetes mellitus. Insulin preparations reliably lower blood glucose levels, but carry the risk of causing hypoglycemia. Sulfonylurea preparations are drugs that lower blood glucose levels by enhancing endogenous insulin secretion by stimulating pancreatic β-cells. Sulfonylurea preparations may cause hypoglycemia as a side effect due to the secretion of insulin that is induced irrespective of blood glucose levels. Biguanide preparations are drugs that lower blood glucose levels by inhibiting gluconeogenesis in the liver, increasing sugar consumption in the skeletal muscles etc., and inhibiting intestinal absorption of sugars. Biguanide preparations have the advantage of not causing hypoglycemia in either normal subjects or diabetic patients, but are likely to cause comparatively severe lactic acidosis. Insulin resistance improvers (e.g., thiazolidine derivatives etc.) are drugs that lower blood glucose levels by increasing the action of insulin and activating insulin receptor kinases. However, the following problems of insulin resistance improvers have been pointed out: digestive symptoms, edema, etc. develop as side effects; the amounts of red blood cells, hematocrit and hemoglobin are decreased; and the amount of LDH is increased (Non-Patent Literature (NPL) 2). α-Glucosidase inhibitors exhibit an effect of inhibiting an increase in after-meal blood glucose level by retarding the digestion and absorption of sugars in the gastrointestinal tract, but have problematic side effects such as a bloated sensation, borborygmus, and diarrhea (Non-Patent Literature (NPL) 3).

Thus, a decisive method for effectively treating or preventing diabetes and diabetic complications has yet to be established.

Recently, peptides that have an effect of inhibiting an increase in blood glucose level (i.e., an inhibitory effect on an increase in blood glucose level) and an effect of enhancing insulin secretion (an insulin secretion-enhancing effect) have been receiving attention. For example, Patent Literatures (PTLs) 1 to 3 suggest using such a peptide as an active ingredient of antidiabetics.

CITATION LIST

Patent Literature

PTL 1: Japanese Unexamined Patent Publication No. 2007-524584
PTL 2: WO 2003/030936
PTL 3: Japanese Unexamined Patent Publication No. 2008-519758

Non-Patent Literature

NPL 1: "Saishin Igaku Daijiten", 1988, p. 1211, Ishiyaku Publishers Inc., Japan
NPL 2: "Atarashii Tonyobyo Chiryoyaku (New Diabetic Medicines)", pp. 90-99, 1994, Iyaku (Medicine and Drug) Journal Co., Ltd., Japan
NPL 3: Joslin's Diabetes mellitus, 13th ed., pp. 521-522.

SUMMARY OF INVENTION

Technical Problem

An object of the present invention is to provide a novel peptide that has an inhibitory effect on an increase in blood glucose level, or an insulin secretion-enhancing effect. Another object of the present invention is to provide a pharmaceutical composition, food and beverage compositions, or feed composition comprising the above peptide as an active ingredient, and thereby exhibiting an inhibitory effect on an increase in blood glucose level, or an insulin secretion-enhancing effect. A further object of the present invention is to provide such a composition as a composition for inhibiting an increase in blood glucose level, a composition for enhancing insulin secretion, or a composition for treating or preventing diabetes or diabetic complications.

Solution to Problem

The present inventors conducted extensive research to achieve the objects described above. The inventors found that when a tetrapeptide (Leu-Ser-Glu-Leu) (SEQ ID NO:1) is administered to mice with artificially induced hyperglycemia, the blood glucose level is significantly lowered and the hyperglycemia is ameliorated. The inventors conducted further research, and confirmed that the blood glucose increase inhibitory effect of the LSEL peptide is due to an insulin secretion-enhancing effect.

Based on the above findings, the inventors confirmed that the LSEL peptide inhibits and ameliorates hyperglycemia (lowers hyperglycemic blood glucose level) in diabetic patients or borderline diabetic patients, i.e., prediabetic patients, and is effective for preventing or treating diseases caused by hyperglycemia, such as diabetes and diabetic complications. The present invention was accomplished based on these findings.

More specifically, the present invention includes the following embodiments.

(I) Novel Peptide

A peptide consisting of an amino acid sequence represented by Leu-Ser-Glu-Leu (SEQ ID NO:1).

(II) Composition (II-1) A pharmaceutical composition, food and beverage compositions, or feed composition comprising the peptide of Item (I) as an active ingredient.

(II-2) A composition for inhibiting an increase in blood glucose level, the composition comprising the peptide of Item (I) as an active ingredient.

(II-3) A composition for enhancing insulin secretion, the composition comprising the peptide of Item (I) as an active ingredient.

(II-4) A composition for preventing or treating a disease caused by hyperglycemia, the composition comprising the peptide of Item (I) as an active ingredient.

(II-5) The composition according to Item (II-4), wherein the disease caused by hyperglycemia is diabetes or a diabetic complication.

(II-6) The composition according to Item (II-5), wherein the diabetic complication is at least one disease selected from the group consisting of diabetic acidosis, diabetic xanthoma, diabetic amyotrophy, diabetic ketosis, diabetic coma, diabetic gastric disorder, diabetic gangrene, diabetic ulcer, diabetes related complications, diabetic diarrhea, diabetic microangiopathy, diabetic uterine body sclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, and diabetic blood circulation disorder.

(II-7) The composition according to Item (II-5) or (II-6), wherein the diabetes is type 2 diabetes.

(III) Method of Treating or Preventing a Disease Caused by Hyperglycemia (III-1) A method of treating or preventing a disease caused by hyperglycemia, comprising administering the composition of any one of Items (II-1) to (II-7) to a patient with a disease caused by hyperglycemia.

(III-2) The method according to Item (III-1), wherein the disease caused by hyperglycemia is diabetes or a diabetic complication.

(III-3) The method according to Item (III-2), wherein the diabetic complication is diabetic acidosis, diabetic xanthoma, diabetic amyotrophy, diabetic ketosis, diabetic coma, diabetic gastric disorder, diabetic gangrene, diabetic ulcer, diabetes related complications, diabetic diarrhea, diabetic microangiopathy, diabetic uterine body sclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, and diabetic blood circulation disorder.

(III-4) The method according to Item (III-2) or (III-3), wherein the diabetes is type 2 diabetes.

(IV) Use of Peptide (IV-1) Use of a peptide consisting of an amino acid sequence represented by Leu-Ser-Glu-Leu (SEQ ID NO:1) to produce a composition for preventing or treating a disease caused by hyperglycemia.

(IV-2) The use according to Item (IV-1), wherein the disease caused by hyperglycemia is diabetes or a diabetic complication.

(IV-3) The use according to Item (IV-2), wherein the diabetic complication is at least one disease selected from the group consisting of diabetic acidosis, diabetic xanthoma, diabetic amyotrophy, diabetic ketosis, diabetic coma, diabetic gastric disorder, diabetic gangrene, diabetic ulcer, diabetes related complications, diabetic diarrhea, diabetic microangiopathy, diabetic uterine body sclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, and diabetic blood circulation disorder.

(IV-4) The use according to Item (IV-2) or (IV-3), wherein the diabetes is type 2 diabetes.

(IV-5) A peptide consisting of an amino acid sequence represented by Leu-Ser-Glu-Leu (SEQ ID NO:1) for use in prevention or treatment of a disease caused by hyperglycemia.

(IV-6) The peptide according to Item (IV-5), wherein the disease caused by hyperglycemia is diabetes or a diabetic complication.

(IV-7) The peptide according to (IV-6), wherein the diabetic complication is at least one disease selected from the group consisting of diabetic acidosis, diabetic xanthoma, diabetic amyotrophy, diabetic ketosis, diabetic coma, diabetic gastric disorder, diabetic gangrene, diabetic ulcer, diabetes related complications, diabetic diarrhea, diabetic microangiopathy, diabetic uterine body sclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, and diabetic blood circulation disorder.

(IV-8) The peptide according to Item (IV-6) or (IV-7), wherein the diabetes is type 2 diabetes.

DESCRIPTION OF EMBODIMENTS (1) Peptide (Leu-Ser-Glu-Leu) (SEQ ID NO:1)

The present invention provides a tetrapeptide consisting of an amino acid sequence represented by Leu-Ser-Glu-Leu (SEQ ID NO:1) (hereinafter sometimes referred to as "the LSEL peptide" or "the peptide of the present invention"). This peptide exhibits an inhibitory effect on an increase in blood glucose level, and an insulin secretion-enhancing effect, when orally or parenterally administered, as demonstrated in the Experimental Examples below using mouse models of diabetes and normal mice with artificially induced hyperglycemia. More specifically, the peptide is a bioactive peptide that has an inhibitory effect on an increase in blood glucose level, as well as an insulin secretion-enhancing effect.

The peptide of the present invention can be synthesized according to the amino acid sequence by general chemical synthesis methods. Such chemical synthesis methods include usual liquid-phase and solid-phase methods. More particularly, examples of peptide synthesis methods include the stepwise elongation method, in which individual amino acids are serially bound one after another according to the amino acid sequence information provided by the present invention; and the fragment condensation method, in which fragments each consisting of several amino acids are synthesized beforehand, and then coupled by a reaction. The peptide of the invention can be synthesized by any of the above methods.

Known condensation methods can be used to synthesize the peptide. Examples of condensation methods include the azide method, mixed acid anhydride method, DCC method, activated ester method, oxidation-reduction method, DPPA (diphenylphosphoryl azide) method, DCC-additive (1-hydroxybenzotriazole, N-hydroxysuccinimide, N-hydroxy-5-norbornene-2,3-dicarboximide, etc.) method, Woodward method, and the like. Solvents that can be used in the above methods may be suitably selected from general solvents that are well known to be used in this type of peptide condensation reaction. Examples of such solvents include dimethylformamide (DMF), dimethyl sulfoxide (DMSO), hexaphosphoramide, dioxane, tetrahydrofuran (THF), ethyl acetate, and mixtures of such solvents.

Carboxyl groups in the peptide or amino acid that are not involved in the peptide synthesis reaction can generally be protected by esterification, for example, in the form of lower alkyl esters such as methyl ester, ethyl ester, and tert-butyl ester, aralkyl esters such as benzyl ester, p-methoxybenzyl ester, p-nitrobenzyl ester, and aralkyl ester, etc. The reaction for removing protective groups from such a protected amino acid, peptide, and the end product peptide of the invention can also be carried out by known methods, such as the catalytic reduction method, or methods using liquid ammonia/sodium, hydrogen fluoride, hydrogen bromide, hydrogen chloride, trifluoroacetic acid, acetic acid, formic acid, methanesulfonic acid, etc.

The peptide of the invention thus obtained can be suitably purified according to methods generally used in the field of peptide chemistry, such as the ion-exchange resin method, partition chromatography, gel chromatography, affinity chromatography, high performance liquid chromatography (HPLC), and the countercurrent distribution method.

In addition to the above-mentioned chemical synthesis methods, the peptide of the invention can also be produced by enzymatic degradation or hydrolysis of a polypeptide or protein comprising the above amino acid sequence (Leu-Ser-Glu-Leu; SEQ ID NO:1). The source of such a polypeptide or protein is not particularly limited, and may be any of animals, fish, shellfish, and plants. For reference, FIG. 1 shows a list of animals, fish, shellfish, and plants containing a polypeptide or protein comprising the amino acid sequence (Leu-Ser-Glu-Leu; SEQ ID NO:1), which is a search result obtained using the amino acid sequence database "FASTA" hosted by the DNA Databank of Japan.

As described above, the LSEL peptide exhibits bioactive effects (pharmacological effects), i.e., an inhibitory effect on an increase in blood glucose level, and an insulin secretion-enhancing effect, when orally or parenterally administered. Therefore, the LSEL peptide is suitable for use as an active ingredient of pharmaceutical compositions, food and beverage compositions, or feed compositions.

Pharmaceutical compositions, food and beverage compositions, and feed compositions that comprise the LSEL peptide as an active ingredient are described below.

(2) Pharmaceutical Composition

A feature of the pharmaceutical composition of the invention is containing the LSEL peptide as an active ingredient.

The pharmaceutical composition provided according to the present invention includes compositions for inhibiting an increase in blood glucose level (blood glucose increase inhibitors); compositions for enhancing insulin secretion (insulin secretion enhancers); and compositions for preventing or treating diseases caused by hyperglycemia (preventive or therapeutic agents for diseases caused by hyperglycemia).

A feature of the compositions for inhibiting an increase in blood glucose level is containing the LSEL peptide in an amount effective for preventing or treating hyperglycemia (inhibiting an increase in blood glucose level) in diabetic patients or borderline diabetic patients, i.e. prediabetic patients. A feature of the compositions for enhancing insulin secretion is containing the peptide LSEL peptide in an amount effective for enhancing insulin secretion in diabetic patients or borderline diabetic patients. Further, a feature of the compositions for preventing or treating diseases caused by hyperglycemia is containing the LSEL peptide in an amount effective for exhibiting the blood glucose increase inhibitory effect or insulin secretion-enhancing effect, and thereby preventing or treating the diseases.

As long as the pharmaceutical composition of the invention contains the LSEL peptide in an amount effective for exhibiting an inhibitory effect on an increase in blood glucose level or an insulin secretion-enhancing effect, the composition may be composed entirely of the LSEL peptide. However, the pharmaceutical composition of the invention is typically prepared concomitantly with pharmacologically acceptable carriers and/or additives.

Examples of carriers include excipients, diluents, binders, humectants, disintegrators, disintegration inhibitors, absorbefacients, lubricants, solubilizers, buffers, emulsifiers, suspending agents, and the like that are typically used according to the dosage form of the pharmaceutical composition (preparation). Examples of additives include stabilizers, preservatives, buffers, isotonizing agents, chelating agents, pH adjusters, surfactants, coloring agents, aroma chemicals, flavoring agents, sweeteners, and the like that are typically used according to the dosage form of the preparation.

The unit dosage form of the pharmaceutical composition (form of the pharmaceutical preparation) of the invention can be suitably selected according to the administration route. The pharmaceutical composition may be roughly classified as an oral agent or parenteral agent (e.g., transpulmonary agent, transnasal agent, sublingual agent, injection, drip, etc.). The pharmaceutical composition can be compounded, formed or prepared according to known methods into solid dosage forms such as tablets, pills, fine powders, powders, granules, and capsules; and liquid dosage forms such as solutions, suspensions, emulsions, syrups, and elixirs. The pharmaceutical composition may be prepared in the form of a dried product that can be liquefied by the addition of a suitable carrier when used. The pharmaceutical composition can be prepared into any of such forms according to known methods.

The amount of LSEL peptide in the pharmaceutical composition of the invention is not particularly limited. The pharmaceutical composition may typically be formed into a pharmaceutical preparation that contains the LSEL peptide in an amount of about 0.1 wt. % to about 80 wt. % according to the dosage form.

The dosage of the pharmaceutical composition obtained in such a manner can be suitably selected according to the purpose of the pharmaceutical composition (inhibition of an increase in blood glucose level, insulin secretion enhancement, prevention or treatment of a disease caused by hyperglycemia); the method of administering the composition; the dosage form; the age, body weight, and symptoms (severity of diabetes) of the patient; and other factors. In general, the LSEL peptide is preferably administered to an adult in a daily dosage of about 10 mg to about 1,000 mg.

The pharmaceutical composition does not have to be administered in a single dose per day, and can be administered in 3 to 4 divided doses per day. The pharmaceutical preparation in such an aforementioned form is administered in a route suitable for the form. For example, the pharmaceutical preparation in an injectable form can be administered intravenously, intramuscularly, subcutaneously, intracutaneously, intraperitoneally, etc.; and the pharmaceutical preparation in a solid form can be administered orally etc.

As demonstrated in the Experimental Examples below, the pharmaceutical composition of the invention has an insulin secretion-enhancing effect due to the LSEL peptide, ameliorates hyperglycemia caused by a reduction or absence of insulin action, and hence exhibits an inhibitory effect on an increase in blood glucose level. Therefore, the pharmaceutical composition of the present invention is effective as a composition for preventing or treating various diseases caused by hyperglycemia caused by the reduction or absence of insulin action.

Such diseases include diabetes and diabetic complications. The target diabetes is preferably non-insulin-dependent (type 2) diabetes.

According to the guidelines (1999) of the Japan Diabetes Society, a patient can be diagnosed as diabetic when the patient has at least one of the following blood glucose levels: a casual glucose level of 200 mg/dL or greater, a fasting glucose level of 126 mg/dL or greater, or a 2-hour post-load glucose level of 200 mg/dL or greater after a 75 g oral glucose tolerance test. Further, a patient can be diagnosed as diabetic when positive results according to the above criteria are obtained twice in tests performed on different days; when a symptom characteristic of diabetes is observed even once; when the concentration of $HbA_{1c}$ (hemoglobin $A_{1c}$) is 6.5% or more; or when diabetic retinopathy is observed. The $HbA_{1c}$ value is an important glycemic control index, and the evaluation is generally made based on this value. The $HbA_{1c}$ value reflects the patient's average blood glucose level over a period of the past 1 to 2 months, and is fairly stable in each patient; therefore, the $HbA_{1c}$ value is the most important indicator of blood glucose control.

The target diabetes of the present invention includes preclinical diabetes (borderline diabetes), in addition to cases diagnosed as diabetics according to the above criteria. A patient can be diagnosed as a borderline diabetic when the patient has a fasting glucose level of from 110 to 125 mg/dL, or a 2-hour post-load glucose level of from 140 to 199 mg/dL after the glucose tolerance test.

Diabetic complications discussed herein refer to systemic and local diseases that directly or indirectly develop along with diabetes (preferably non-insulin-dependent type 2 diabetes). Specific examples are diabetic acidosis, diabetic xanthoma, diabetic amyotrophy, diabetic ketosis, diabetic coma, diabetic gastropathy, diabetic gangrene, diabetic ulcer, diabetes related complications, diabetic diarrhea, diabetic microangiopathy, diabetic uterine body sclerosis, diabetic cardiomyopathy, diabetic neuropathy, diabetic nephropathy, bullosis diabeticorum, diabetic cataract, diabetic dermopathy, diabetic scleredema, diabetic retinopathy, necrobiosis lipoidica diabeticorum, diabetic blood circulation disorder, etc.

The pharmaceutical composition of the present invention can be administered to patients with various diseases caused by hyperglycemic conditions as mentioned above, to thereby effectively prevent or treat the diseases in the patients.

The pharmaceutical composition of the present invention includes pharmaceutical compositions for animals, as well as pharmaceutical compositions for humans.

(3) Food and Beverage Compositions

A feature of the food and beverage compositions of the present invention is containing the LSEL peptide as an active ingredient.

The food and beverage compositions provided according to the present invention include foods and beverages for specified health use (including foods and beverages qualified for specified health use, i.e., qualified FOSHU) that have a function of inhibiting an increase in blood glucose level; foods and beverages for specified health use (including foods and beverages qualified for specified health use, i.e., qualified FOSHU) that have a function of enhancing insulin secretion; and foods and beverages for specified health use (foods and beverages qualified for specified health use, i.e., qualified FOSHU) that are used to prevent or ameliorate diseases caused by hyperglycemia due to blood glucose increase inhibitory effects or insulin secretion-enhancing effects.

A feature of the foods and beverages for specified health use that have a function of inhibiting an increase in blood glucose level is containing the LSEL peptide in an amount effective for preventing or ameliorating a hyperglycemic condition (inhibiting an increase in blood glucose level) in a diabetic patient or a borderline diabetic patient; packaging and advertisements for the foods and beverages may carry notices of the effect (inhibitory effect on an increase in blood glucose level). A feature of the foods and beverages for specified health use that have a function of enhancing insulin secretion is containing the LSEL peptide in an amount effective for enhancing insulin secretion in a diabetic patient or a borderline diabetic patient; packaging and advertisements for the foods and beverages may carry notices of the effect (insulin secretion-enhancing effect). A feature of the foods and beverages for specified health use that are used for preventing or ameliorating diseases caused by hyperglycemia is containing the LSEL peptide in an amount effective for preventing or ameliorating diseases as mentioned above due to the blood glucose increase inhibitory effect or insulin secretion-enhancing effect; and packaging and advertisements for the foods and beverages may carry notices of the effect (antidiabetic effect).

As long as the food and beverage compositions of the invention contain the LSEL peptide in an amount effective for exhibiting an inhibitory effect on an increase in blood glucose level, or an insulin secretion-enhancing effect, the food and beverage compositions of the present invention may be composed entirely of the LSEL peptide. However, the food and beverage compositions of the invention are typically prepared concomitantly with carriers or additives that are usable in foods and beverages. When an LSEL peptide is obtained from animals, fish, shellfish or plants, the LSEL peptide does not always have to be purified, insofar as the obtained peptide has a blood glucose increase inhibitory effect or an insulin secretion-enhancing effect. A proteolysate containing the LSEL peptide or a fraction thereof may also be used as an active ingredient of the food and beverage compositions of the present invention.

The food and beverage compositions of the present invention include food and beverage additives and supplements that are prepared in the form of tablets, pills, capsules, granules, fine powders, powders, solutions (drinks), etc., using the peptide LESL optionally with carriers and additives that are acceptable for foods and beverages. Further, the compositions include products containing the peptide LSEL that may take the form of ordinary foods and beverages.

Examples of such foods and beverages include milk beverages, lactic acid bacteria beverages, fruit juice-containing soft drinks, soft drinks, carbonated beverages, fruit juice drinks, vegetable juice drinks, vegetable/fruit beverages, alcoholic beverages, powdered beverages, coffee beverages, black tea beverages, green tea beverages, barley tea beverages, and like beverages; custard puddings, milk puddings, soufflé puddings, fruit juice-containing puddings and like puddings, jellies, bavarois, yogurt, and like desserts; ice creams, ice milks, lacto-ices, milk ice creams, fruit juice-containing ice creams, soft creams, ice candies, sherbets, frozen confections, and like chilled confections; chewing gums, bubble gums, and like gums (stick gums, sugar-coated tablet gums); marble chocolates and like coated chocolates, strawberry chocolates, blueberry chocolates, melon chocolates and like flavored chocolates, and like chocolates; hard candies (including bonbons, butterballs, marbles, etc.), soft candies (including caramels, nougats, gummy candies, marshmallows, etc.), drops, taffy, and like caramels; hard biscuits, cookies, okaki (rice crackers), sembei (rice crackers), and like baked confections (all of the above are confections); consommé soups, potage soups, and like soups; strawberry jams, blueberry jams, marmalades, apple jams, apricot jams, preserves, like jams; red wines and like fruit wines; syruped cherries, apricots, apples, strawberries and peaches, and like processed fruits; ham, sausage, roast pork, and like processed livestock meat; fish ham, fish sausage, fish fillets, kamaboko (steamed fish paste), chikuwa (baked fish paste), hanpen (minced and steamed fish), satsumaage (fried fish ball), datemaki (omelet wrappers), whale bacon, and like processed marine products; udon (wheat noodles), hiyamugi, (iced noodles), somen (fine noodles), soba (buckwheat noodles), Chinese noodles, spaghetti, macaroni, bifun (rice noodles), harusame (bean-jelly stick), wonton, and like noodles; and various types of side dishes, wheat gluten cake, denbu (mashed and seasoned fish) and like various other processed food products. The food and beverage compositions of the invention are preferably in the form of a beverage or a confection.

The amount of active ingredient (the LSEL peptide) in the food and beverage compositions, or the intake amount of the food and beverage compositions are not particularly limited, and can be suitably selected from a broad range according to the type of the food and beverage compositions, extent of the desired ameliorative effect, and other factors. Although the dosage of the food and beverage compositions may vary depending on the type of the food and beverage compositions, the dosage can be suitably selected from the range of about 10 mg/60 kg body weight to about 1,000 mg/60 kg body weight, calculated as the LSEL peptide per administration to a human having a body weight of 60 kg.

The food and beverage compositions of the present invention exhibit an insulin secretion-enhancing effect due to the LSEL peptide, ameliorates hyperglycemia caused by a reduction or absence of insulin action, and hence inhibits an increase in blood glucose level. Therefore, the food and beverage compositions of the present invention can be effectively used as compositions for preventing or treating various diseases caused by hyperglycemia.

(4) Feed Composition

A feature of the feed composition of the present invention is containing the LSEL peptide as an active ingredient.

The feed composition provided according to the present invention includes feeds that have a function of inhibiting an increase in blood glucose level; feeds that have a function of enhancing insulin secretion; and feeds that are used to prevent or treat diseases caused by hyperglycemia due to the inhibitory effect on an increase in blood glucose level, or the insulin secretion enhancing-effect. Such feeds can be preferably used as pet food, especially for dogs, cats and like animals. A feature of the feeds having the function of inhibiting an increase in blood glucose level is containing the LSEL peptide in an amount effective for preventing or ameliorating a hyperglycemic condition (inhibiting an increase in blood glucose level) in a diabetic or prediabetic animal. A feature of the feeds having the function of enhancing insulin secretion is containing the LSEL peptide in an amount effective for enhancing insulin secretion in a diabetic or prediabetic animal. A feature of the feeds that are used to prevent or treat diseases caused by hyperglycemia is containing the LSEL peptide in an amount effective for exhibiting an effect of inhibiting an increase in blood glucose level or enhancing insulin secretion.

The feed composition of the present invention includes those prepared in the form of tablets, pills, capsules, granules, fine powders, powders, solutions, etc., using the LSEL peptide optionally with carriers and additives that can be used in feeds. Further, the composition includes products containing the peptide LSEL that may take the form of ordinary feeds. When an LSEL peptide is obtained from animals, fish, shellfish, or plants, the LSEL peptide does not always have to be purified, insofar as the obtained peptide has a blood glucose increase inhibitory effect or an insulin secretion-enhancing effect. A proteolysate containing the LSEL peptide or a fraction thereof may also be used as an active ingredient of the feed composition of the present invention.

The amount of active ingredient (the LSEL peptide) contained in the feed composition, or the intake amount of the feed composition, is not limited, and can be suitably selected from a broad range according to the type of the feed composition, the kind of animal that ingests the feed composition, the extent of the desired ameliorative effect, and other factors. Although the dosage of the feed composition may vary depending on the type of the feed composition, the dosage can be suitably selected from the range of about 1 mg/10 kg body weight to about 100 mg/10 kg body weight, calculated as the LSEL peptide per administration to an animal having a body weight of 10 kg.

EXAMPLES

Preparation Examples and Experimental Examples are given below to illustrate the invention in more detail. However, the scope of the invention is not limited by the Experimental Examples. In the Experimental Examples below, "%" represents "percent by weight", unless specified otherwise.

Preparation Example 1

Synthesis of LSEL Peptide

A peptide consisting of the amino acid sequence Leu-Ser-Glu-Leu (SEQ ID NO: 1) (LSEL peptide) was synthesized by a standard liquid phase method (more specifically, the present inventors outsourced production of the peptide to Shanghai C-Strong Co., Ltd. (Shanghai, China)). The amino acid sequence of the obtained peptide was analyzed by the liquid phase automated Edman degradation method (apparatus: a Procise HT protein sequencing system manufactured by Applied Biosystems). The results confirmed that the obtained peptide is a tetrapeptide consisting of the amino acid sequence shown above.

Experimental Example 1

Effect of Oral or Subcutaneous Administration of the LSEL Peptide on Blood Glucose Level in Glucose-Loaded Normal Mice The LSEL peptide prepared in Preparation Example 1 was orally or subcutaneously administered to glucose-loaded normal mice to examine the effects of the peptide on blood glucose levels in the mice. In this test, 7-week old male ICR mice (Japan SLC) were used.

First, the blood glucose levels in the mice, which were fasted overnight (for about 18 hours), were measured. Based on the obtained blood glucose levels, the mice were divided into 6 groups: (3 groups as LSEL oral administration groups; 1 group as an LSEL subcutaneous administration group; 1 group as an oral administration control group; and 1 group as a subcutaneous administration control group). Table 1 shows the dosage of the LSEL peptide, administration route, and the number of mice in the LSEL oral administration groups and LSEL subcutaneous administration group.

To the LSEL oral administration groups, glucose (2 g/kg body weight) and the LSEL peptide (10 mg/kg body weight, 25 mg/kg body weight, or 50 mg/kg body weight) were mixed and orally administered simultaneously, and their blood glucose levels were measured 30 minutes, 60 minutes, 90 minutes, and 120 minutes after the administration. To the LSEL subcutaneous administration group, the LSEL peptide (25 mg/kg body weight) was subcutaneously administered immediately after the oral administration of glucose (2 g/kg body weight), and their blood glucose levels were measured 30 minutes, 60 minutes, 90 minutes, and 120 minutes after the administration. To the oral administration control group (n=24), glucose (2 g/kg body weight) and distilled water were mixed and orally administered simultaneously. To the subcutaneous administration control group (n=11), physiological saline was subcutaneously administered immediately after the oral administration of glucose (2 g/kg body weight), and their blood glucose levels were measured 30 minutes, 60 minutes, 90 minutes, and 120 minutes after the administration. Specifically, glucose was used in the form of a solution by dissolving glucose in physiological saline, and administering the solution in a volume of 10 mL/kg body weight (the same applies to the experiments described below); and the blood glucose levels were determined by a compact blood glucose measuring device "Caresist" (manufactured by Roche) using one drop of blood collected from the tail vein of each mouse.

FIG. 2 shows the changes in blood glucose level over time in an LSEL oral administration group (dosage of the LSEL peptide: 50 mg/kg body weight) and in the control group. FIG. 3 shows the changes in blood glucose level over time in the LSEL subcutaneous administration group (dosage of LSEL peptide: 25 mg/kg body weight) and in the control group. The area under the concentration versus time curve from 0 to 2 hours ($AUC_{0-2h}$) in each group was obtained, and the blood glucose $AUC_{0-2h}$ suppression (%) was calculated according to the following formula. Table 1 shows the results.

$$\text{Blood glucose } AUC_{0-2h} \text{ suppression (\%)} = \frac{\left\{ (AUC_{0-2h} \text{ of the control group}^*) - \left( \begin{array}{c} AUC_{0-2h} \text{ of the } LSEL \text{ peptide} \\ \text{administration group}^* \end{array} \right) \right\}}{(AUC_{0-2h} \text{ of the control group}*)} \times 100 \quad \text{[Mathematical Formula 1]}$$

Notes:
Control group*: Control group (oral administration group, subcutaneous administration group) LSEL peptide administration group*: LSEL peptide administration group (oral administration group, subcutaneous administration group)

TABLE 1

| Test substance | Dosage (mg/kg) | Administration route | Number of mice | Blood glucose $AUC_{0-2h}$ suppression (%) |     |
|---|---|---|---|---|---|
| LSEL | 10 | Oral | 12 | 1.7 | |
|      | 25 | Oral | 18 | 7.4 | |
|      | 50 | Oral | 24 | 13.2 | p < 0.1 |
|      | 25 | Subcutaneous | 11 | 23.2 | p < 0.05 |

FIG. 2 and Table 1 clearly show that oral administration of the LSEL peptide to glucose-loaded normal mice, dose-dependently suppressed an increase in blood glucose level. Particularly, administration of the LSEL peptide in an amount of 50 mg/kg reduced the area under the concentration versus time curve by 13.2% (P<0.1), compared to the control group. FIG. 3 and Table 1 clearly show that subcutaneous administration of the LSEL peptide (25 mg/kg body weight) to glucose-loaded normal mice reduced the area under the concentration versus time curve by 23.2% (P<0.05), compared to the control group.

The above results clearly show that the LSEL peptide can suppress an increase in blood glucose level, whether the peptide is administered orally or subcutaneously.

Experimental Example 2

Effect of Oral Administration of the LSEL Peptide on Blood Glucose Level in Glucose-Loaded KK-Ay-Mouse Models of Type 2 Diabetes The LSEL peptide prepared in Preparation Example 1 was orally administered to glucose-loaded KK-Ay-mouse models of type 2 diabetes. In this test, 9-week old male KK-Ay mouse models of type 2 diabetes (CLEA Japan, Inc.) were used.

More specifically, the blood glucose levels in the mice, which were fasted overnight (for about 18 hours), were measured. Based on the obtained blood glucose levels, the mice were divided into 4 groups: (3 groups as LSEL oral administration groups, and 1 group as a control group). Table 2 shows the dosage of the LSEL peptide, and the number of mice in each LSEL oral administration group. To the LSEL oral administration groups, glucose (2 g/kg body weight) and the LSEL peptide (25 mg/kg body weight, 50 mg/kg body weight, or 100 mg/kg body weight) were mixed and orally administered simultaneously, and their blood glucose levels were measured 30 minutes, 60 minutes, 90 minutes, and 120 minutes after the administration. To the control group (n=11), glucose (2 g/kg body weight) and distilled water were mixed and orally administered simultaneously, and their blood glucose levels were measured was measured 30 minutes, 60 minutes, 90 minutes, and 120 minutes after the administration. Specifically, glucose was used in the form of a solution by dissolving glucose in physiological saline and administering the solution in an amount of 10 mL/kg body weight; and the blood glucose levels were measured by "Caresist" (manufactured by Roche) using one drop of blood collected from the tail vein of each mouse.

FIG. 4 shows the changes in blood glucose level over time in the LSEL oral administration group (LSEL peptide dosage: 100 mg/kg body weight) and in the control group. The area under the concentration versus time curve from 0 to 2 hours ($AUC_{0-2h}$) in each group was determined, and the blood glucose $AUC_{0-2h}$ suppression (%) was calculated according to Mathematical Formula 1 above. Table 2 shows the results.

TABLE 2

| Test substance | Dosage (mg/kg) | Number of mice | Blood glucose $AUC_{0-2h}$ suppression (%) |
|---|---|---|---|
| LSEL | 25 | 5 | 3.6 |
|  | 50 | 11 | 8.8 |
|  | 100 | 11 | 15.3  $p < 0.1$ |

FIG. 4 and Table 2 clearly show that oral administration of the LSEL peptide to mouse models of type 2 diabetes dose-dependently suppressed an increase in blood glucose level. Particularly, administration of the LSEL peptide in an amount of 100 mg/kg reduced the area under the concentration versus time curve by 15.3% (P<0.1), compared to the control group.

A combination of the results of Test Examples 1 and 2 clearly show that administration of the LSEL peptide can significantly suppress an increase in blood glucose level in glucose-loaded normal mice (ICR mice) and in glucose-loaded mouse models of type 2 diabetes (KK-Ay mice), compared to the control groups.

Experimental Example 3

Effect of Oral Administration of the LSEL Peptide on Blood Glucose Level in Sucrose-Loaded ICR Mouse Models The LSEL peptide prepared in Preparation Example 1 was orally administered to sucrose-loaded normal mice to examine the effects of the LSEL peptide on blood glucose levels in the mice. In this test, 7-week old male ICR mice (Japan SLC) were used.

More specifically, the blood glucose levels of the mice, which were fasted overnight for about 18 hours, were measured. Based on the obtained blood glucose levels, the mice were divided into 2 groups: (1 group as an LSEL oral administration group, and 1 group as a control group). Table 3 shows the dosage of the LSEL peptide, and the number of mice in the LSEL oral administration group.

To the LSEL oral administration group, sucrose (2 g/kg body weight) and the LSEL peptide (25 mg/kg body weight) were mixed and orally administered simultaneously, and their blood glucose level was measured 30 minutes, 60 minutes, 90 minutes, and 120 minutes after the administration. To the control group (n=11), sucrose (2 g/kg body weight) and distilled water were mixed and orally administered simultaneously, and their blood glucose levels were measured 30 minutes, 60 minutes, 90 minutes, and 120 minutes after the administration. Stated more specifically, the blood glucose levels were measured by "Caresist" (manufactured by Roche) using one drop of blood collected from the tail vein of each mouse.

FIG. 5 shows the changes in blood glucose level over time in the LSEL oral administration group and in the control group. The area under the concentration versus time curve from 0 to 2 hours ($AUC_{0-2h}$) in each group was obtained, and the blood glucose $AUC_{0-2h}$ suppression (%) was calculated according to Mathematical Formula 1 above. Table 3 shows the results.

TABLE 3

| Test substance | Dosage (mg/kg) | Number of mice | Blood glucose $AUC_{0-2h}$ suppression (%) |
|---|---|---|---|
| LSEL | 25 | 12 | 22.9  $p < 0.05$ |

FIG. 5 and Table 3 clearly show that oral administration of the LSEL peptide to the sucrose-loaded normal mice dose-dependently suppressed an increase in blood glucose level. Particularly, administration of the LSEL peptide in an amount of 25 mg/kg reduced the area under the concentration versus time curve by 22.9% (P<0.05), compared to the control group.

A combination of the results in Test Examples 1 and 3 clearly show that oral administration of the LSEL peptide can significantly suppress an increase in blood glucose level caused by sucrose loading, as well as the increase caused by glucose loading.

Test Example 4

Effect of Oral Administration of the LSEL Peptide on Plasma Insulin Concentration in Glucose-Loaded ICR Mice The LSEL peptide prepared in Preparation Example 1 was orally administered to glucose-loaded normal mice to examine the effects of the peptide on the plasma insulin concentrations in the mice. In this test, 7-week old male ICR mice (Japan SLC) were used.

More specifically, the blood glucose levels of the mice, which were fasted overnight for about 18 hours, were measured. Based on the obtained blood glucose levels, the mice were divided into 2 groups: (one LSEL oral administration group and one control group). Table 4 shows the dosage of the LSEL peptide, and the number of mice in the LSEL oral administration group.

To the LSEL oral administration group, glucose (2 g/kg body weight) and LSEL peptide (50 mg/kg body weight) were mixed and orally administered simultaneously, and their plasma insulin concentrations were measured 15 minutes, 30 minutes, 60 minutes, 90 minutes, and 120 minutes after the administration. To the control group (n=6), glucose (2 g/kg body weight) and distilled water were mixed and orally administered simultaneously, and their plasma insulin concentration was measured 15 minutes, 30 minutes, 60 minutes, 90 minutes, and 120 minutes after the administration. More specifically, the plasma insulin concentration was measured in the following manner. Blood was collected from the eye socket using heparin, and centrifuged to obtain plasma. The insulin concentration in the plasma was measured using an ELISA insulin kit ("Rebis Insulin-Mouse-T", manufactured by Shibayagi Co., Ltd.).

FIG. 6 shows the changes in plasma insulin concentration over time in the LSEL oral administration group and in the control group. The area under the concentration versus time curve from 0 to 2 hours ($AUC_{0-2h}$) in the LSEL oral administration group was obtained, and the increase (%) in insulin $AUC_{0-2h}$ was calculated according to the following formula. Table 1 shows the results.

[Math Formula 2]
$$\text{Increase (\%) in insulin } AUC_{0-2h} = \frac{\left(\begin{array}{c} AUC_{0-2h} \text{ of the } LSEL \\ \text{peptide administration group} \end{array}\right)}{(AUC_{0-2h} \text{ of the control group})} \times 100$$

Table 4 shows the results.

TABLE 4

| Test substance | Dosage (mg/kg) | Number of mice | Increase in insulin $AUC_{0-2h}$ (%) |
|---|---|---|---|
| LSEL | 50 | 7 | 252.0 p < 0.05 |

FIG. 6 and Table 4 clearly show that oral administration of the LSEL peptide in an amount of 50 mg/kg increased the area under the plasma insulin concentration versus time curve from 0 to 2 hours by 252.0% (p<0.05), compared to the control group.

A combination of the results in Test Examples 1 and 4 indicates that LSEL peptide most likely suppresses an increase in blood glucose level due to the insulin secretion-enhancing effect.

Experimental Example 5

Safety

No toxicity was exhibited, even when the LSEL peptide prepared in Preparation Example 1 was orally administered to mice in an amount of 2 g/kg body weight. The results revealed that the $LD_{50}$ of the LSEL peptide is much greater than 2 g/kg body weight.

Example 1

Green Tea Beverage

Eight kilograms of green tea leaves was added to 300 L of hot water (80° C.), and extracted at that temperature for 4 minutes. The resulting extract was cooled, and then centrifuged. Clear supernatant was collected as a green tea extract. To this extract was added 0.4 kg of vitamin C, and then 50 g of the LSEL peptide prepared in Preparation Example 1. Hot water was added to make a final volume of 1,000 L. The resulting mixture was heated to 85° C. or higher, charged into metal cans and retort-sterilized (125° C., 5 minutes), thereby giving a green tea beverage.

Example 2

Tablet

The ingredients shown below were kneaded, granulated, dried, and then tableted according to a standard method, thereby producing tablets containing the LSEL peptide in an amount of 5 wt. % (10 mg) per tablet (200 mg). These tablets are for use as pharmaceutical preparations or supplements having pharmacological effects of the LSEL peptide (inhibitory effect on an increase in blood glucose level, insulin secretion-enhancing effect, antidiabetic effect).

| <Formulation> | (per tablet) |
|---|---|
| Peptide LSEL (prepared in Preparation Example 1) | 50 mg |
| Sorbitol | 190 mg |
| Sucrose fatty acid ester | 10 mg |
| Total | 250 mg |

Example 3

Feed

The LSEL peptide prepared in Preparation Example 1 was added in an amount of 0.1 wt. % to a premix containing vitamins, minerals, and the like. This mixture was added to a commercially available dog food in a amount of 10 wt. %, thereby producing a dog food having an insulin secretion-enhancing effect or an inhibitory effect on an increase in blood glucose level.

INDUSTRIAL APPLICABILITY

According to the present invention, a pharmaceutical composition, food and beverage compositions, or feed composition can be provided that exhibits an inhibitory effect on an increase in blood glucose level or an insulin secretion-enhancing effect due to the peptide (LSEL; SEQ ID NO:1) contained as an active ingredient. These compositions have an effect of lowering hyperglycemic blood glucose levels in diabetic or prediabetic subjects (including humans and animals) due to the blood glucose increase inhibitory effect or insulin secretion-enhancing effect. Therefore, the compositions of the present invention are effective for preventing or treating diseases caused by hyperglycemia, in particular, diabetes and diabetic complications.

BRIEF DESCRIPTION OF THE DRAWINGS

FIG. 1 is a list of animals, fish, shellfish, and plants having a polypeptide or a protein comprising the amino acid sequence (Leu-Ser-Glu-Leu; SEQ ID NO:1).

SEQUENCE LISTING FREE TEXT

Figure 2:
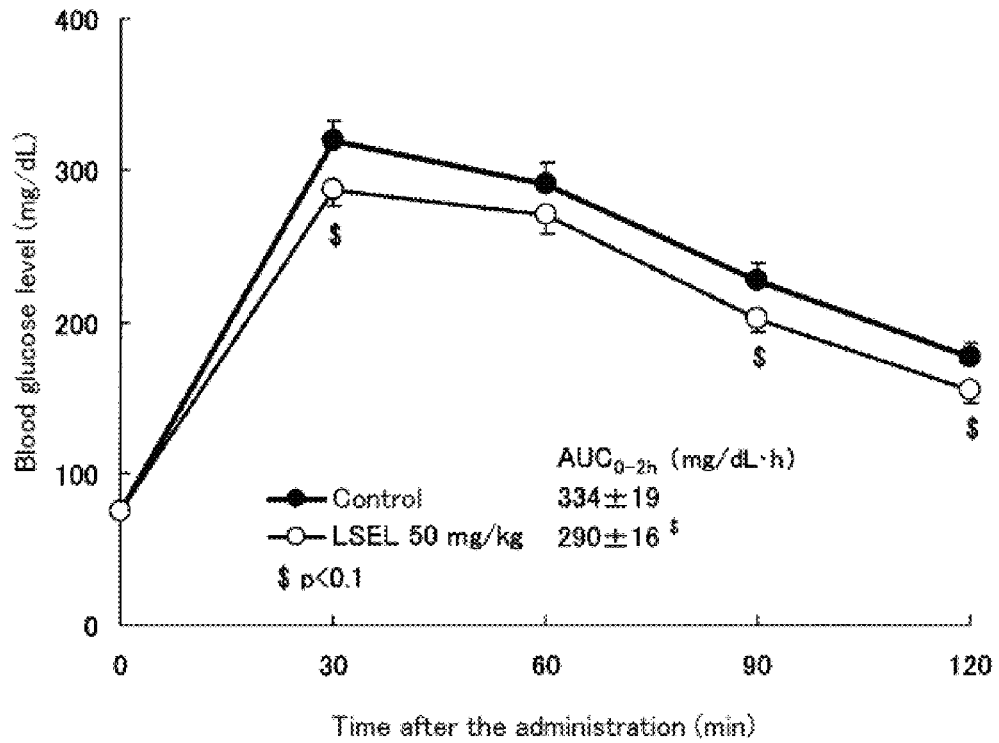
FIG. 2 shows the changes in blood glucose level in glucose-loaded ICR mice, when LSEL (SEQ ID NO:1) was orally administered in Test Example 1.
Figure 3:
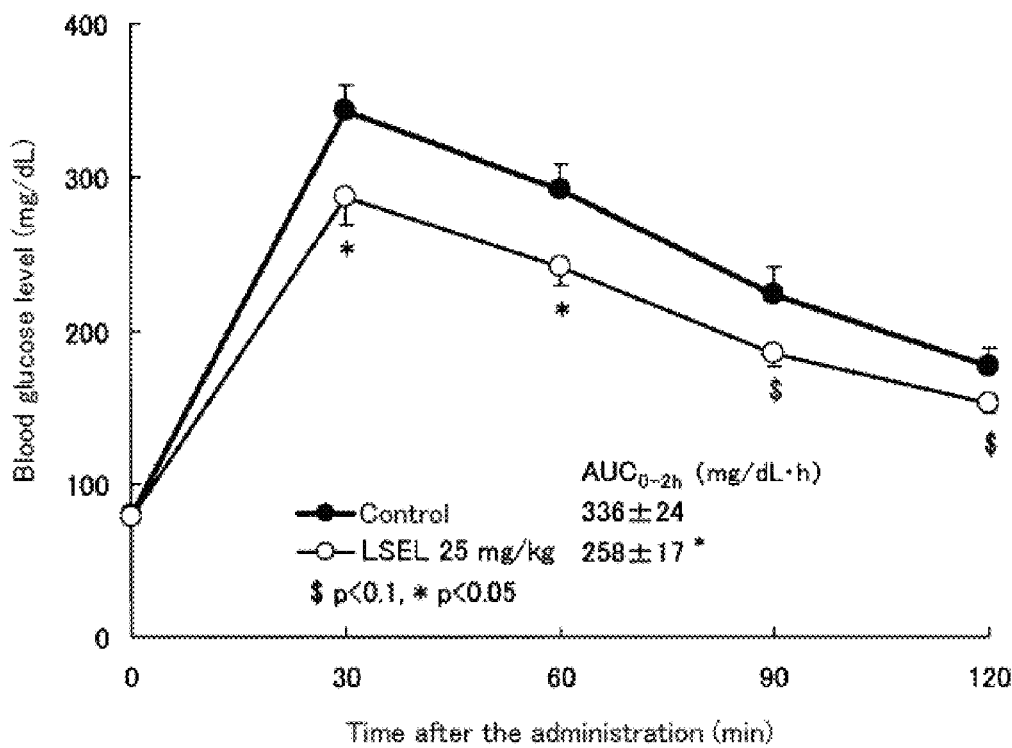
FIG. 3 shows the changes in blood glucose level in glucose-loaded ICR mice, when LSEL (SEQ ID NO:1) was subcutaneously administered in Experimental Example 1.
Figure 4:
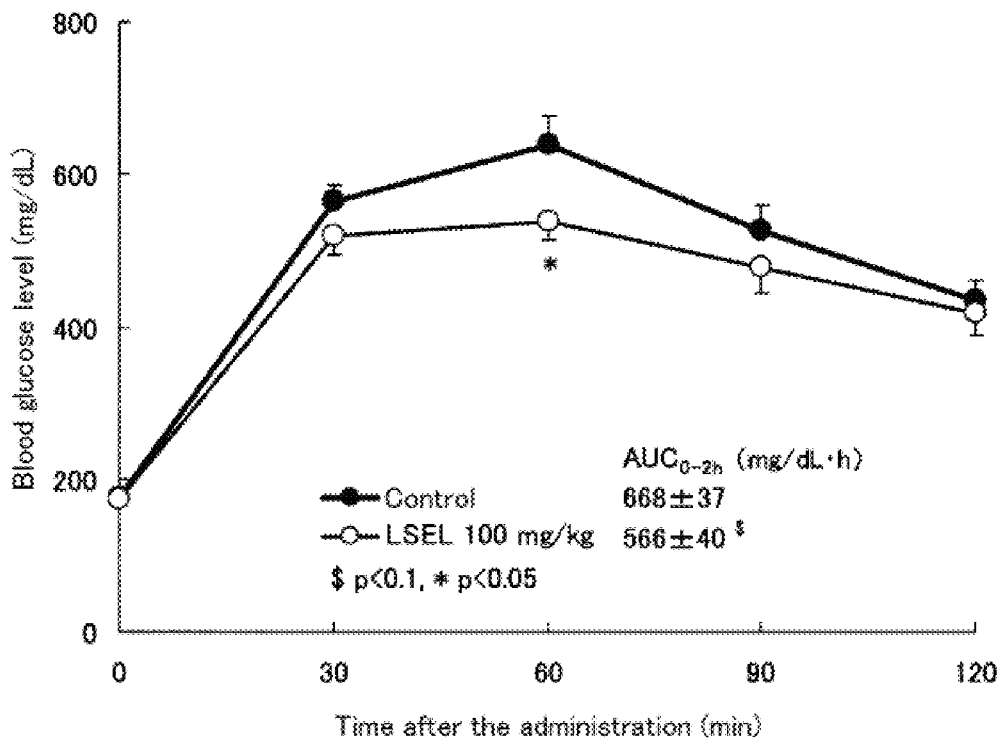
FIG. 4 shows the changes in blood glucose level in glucose-loaded KK-Ay mice, when LSEL (SEQ ID NO:1) was orally administered in Experimental Example 2.
Figure 5:
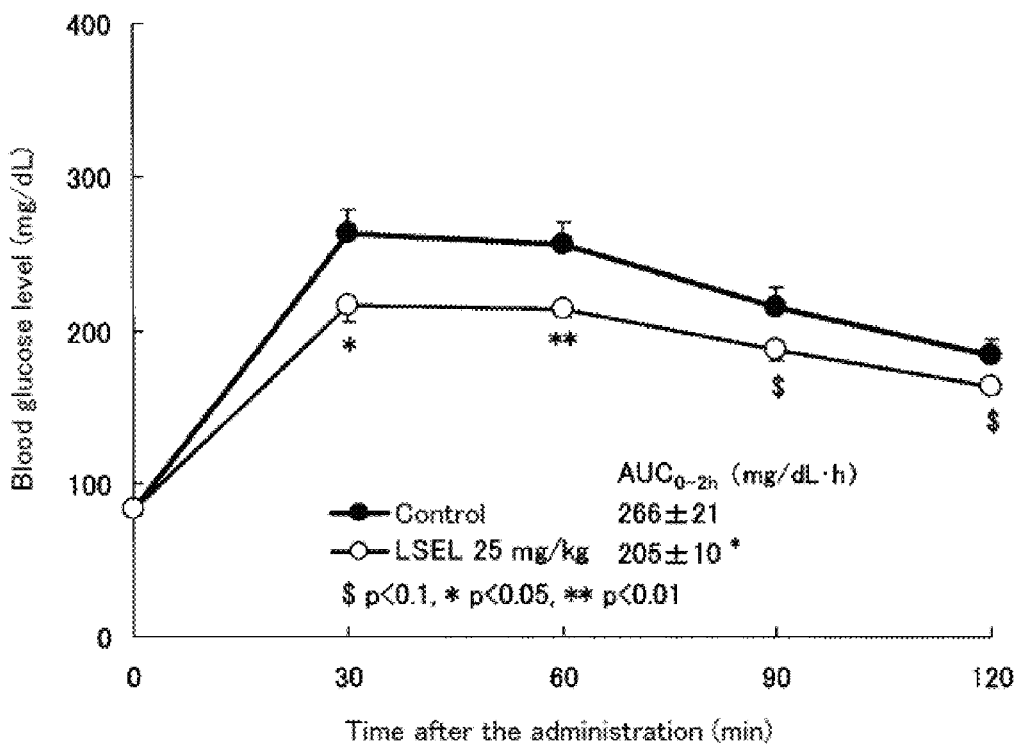
FIG. 5 shows the changes in blood glucose level in sucrose-loaded ICR mice, when LSEL (SEQ ID NO:1) was orally administered in Experimental Example 3.
Figure 6:
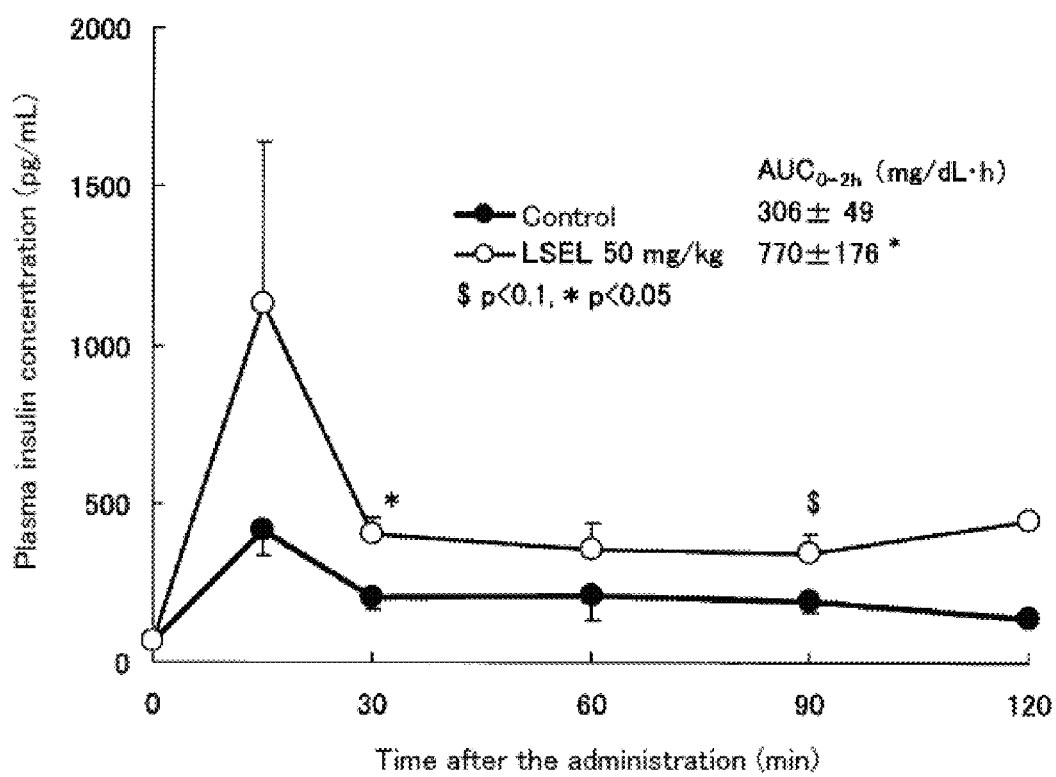
FIG. 6 shows the changes in plasma insulin concentration in glucose-loaded ICR mice, when LSEL (SEQ ID NO:1) was orally administered in Experimental Example 4.

SEQ ID NO: 1 shows the amino acid sequence of a novel tetrapeptide.

The invention claimed is:

1. An isolated peptide consisting of the amino acid sequence represented by Leu-Ser-Glu-Leu (SEQ ID NO:1).

2. A pharmaceutical composition, food and beverage compositions, or feed composition comprising the peptide of claim 1 as an active ingredient.

3. A method of treating type 2 diabetes, comprising administering a pharmaceutical composition or food and beverage compositions comprising the peptide of claim 1 as an active ingredient to a patient having type 2 diabetes.

* * * * *

```
                        SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Novel tetrapeptide

<400> SEQUENCE: 1

Leu Ser Glu Leu
```